United States Patent [19]

Schmidt et al.

[11] Patent Number: 5,506,216
[45] Date of Patent: Apr. 9, 1996

[54] CYCLODEXTRIN-BIOCIDE COMPLEX

[75] Inventors: Axel Schmidt, Müchen; Herbert von der Eltz, Weilheim; Klaus Kaluza, Bad Heilbrunn, all of Germany

[73] Assignee: Boehringer Mannheim GmbH, Mannheim, Germany

[21] Appl. No.: 231,170

[22] Filed: Apr. 22, 1994

[30] Foreign Application Priority Data

Apr. 23, 1993 [DE] Germany .................. 43 13 408.4

[51] Int. Cl.$^6$ .................. C08B 37/16; A01N 31/08; C09K 15/04; C07K 15/06; C10Q 1/00
[52] U.S. Cl. .................. 514/58; 435/7.1; 536/103
[58] Field of Search .................. 536/103; 514/58; 435/7.1

[56] References Cited

U.S. PATENT DOCUMENTS

| | | | |
|---|---|---|---|
| H811 | 8/1990 | Nasu et al. | 514/92 |
| 3,846,551 | 11/1974 | Mifune et al. | 536/103 |
| 3,949,086 | 4/1976 | Wolfson | 536/103 |
| 4,518,610 | 5/1985 | Umekawa et al. | 514/516 |
| 4,524,068 | 6/1985 | Szejtli et al. | 514/58 |
| 4,636,343 | 1/1987 | Shibanai | 264/118 |
| 4,675,395 | 6/1987 | Fukazawa et al. | 536/103 |
| 4,722,815 | 2/1988 | Shibanai | 264/117 |
| 4,725,657 | 2/1988 | Shibanai | 523/210 |
| 4,774,329 | 9/1988 | Friedman | 536/103 |
| 4,847,151 | 7/1989 | Ichiro | 428/389 |
| 4,869,904 | 9/1989 | Uekama et al. | 424/400 |
| 4,883,785 | 11/1989 | Chow et al. | 514/58 |
| 4,923,853 | 5/1990 | Szejtli et al. | 514/58 |
| 5,134,127 | 7/1992 | Stella et al. | 514/58 |
| 5,190,932 | 3/1993 | Dhein et al. | 514/367 |
| 5,300,424 | 4/1994 | Hoss et al. | 435/7.1 |

FOREIGN PATENT DOCUMENTS

| | | |
|---|---|---|
| 0186146 | 7/1986 | European Pat. Off. . |
| 0215169 | 3/1987 | European Pat. Off. . |
| 0306455 | 3/1989 | European Pat. Off. . |
| 0467337A2 | 1/1992 | European Pat. Off. . |

OTHER PUBLICATIONS

WO86/03939 published Jul. 17, 1986.
Derwent Publications Ltd., AN: 84–185578.
Derwent Publications Ltd., AN: 83–767169.

*Primary Examiner*—Ronald W. Griffin
*Attorney, Agent, or Firm*—Nikaido, Marmelstein, Murray & Oram

[57] ABSTRACT

The invention concerns a complex of cyclodextrin and an organic biocide, wherein the organic biocide has a maximum water-solubility of 0.15% (w/v) at a temperature of 25° C., a process for the production of the complex as well as the use of the complex for preserving aqueous solutions. In addition the invention concerns a diagnostic test solution which contains at least one complex according to the invention and a preserved diagnostic test kit which comprises test reagents and at least one complex according to the invention.

11 Claims, No Drawings

CYCLODEXTRIN-BIOCIDE COMPLEX

The present invention concerns new complexes of cyclodextrins and an organic biocide, a process for the production of such complexes as well as the use of the complexes to preserve aqueous solutions, in particular diagnostic test solutions. The present invention in addition concerns a diagnostic test solution which contains at least one of the new cyclodextrin-biocide complexes.

Biological, in particular diagnostic test kits usually contain substances as reagents and standards which can be decomposed by microorganisms. These test kits must therefore contain a preservative in order to improve their stability. However, it has hitherto proven to be extremely difficult to find suitable preservatives for such diagnostics since in addition to an adequate effectiveness towards bacteria, yeasts and fungi, the preservative should not interfere with the reactivity of substances present in the test. The sensitivity of proteins such as e.g. enzymes or antibodies as well as antigens and substrates towards preservatives is demonstrated for example by the fact that the proteins can become denatured or that immunogenic structures can be destroyed. Moreover added preservatives often bind to test substances and in this way represent a competitor to the actual binding partner in the test (e.g. binding of enzyme/substrate, antibody/antigen). Therefore for each specific diagnostic test it was previously necessary to find a preservative in each case which is exactly suitable for this specific test and which has the aforementioned properties. It is clearly apparent that such a search for suitable preservatives is time-consuming and very costly.

A further prerequisite for the use of preservatives in aqueous solutions is naturally an adequately high water-solubility. Most of the conventional biocides are organic compounds. A large number of such biocides is described for example in "K. H. Wallhäußer, "Praxis der Sterilisation, Desinfektion-Konservierung, Georg Thieme Verlag, Stuttgart, New York".

However, a disadvantage of most of the highly effective organic biocides for an application in aqueous solutions such as diagnostic test solutions is that they often have an extremely low water solubility. These biocides can only be used in aqueous solutions by additives such as detergents, organic solvents or by preparing emulsions or dispersions. However, these additives and formulations often lead to undesired interactions and precipitations in diagnostic tests when sensitive substances such as proteins are present which makes it impossible to use these biocides.

Thus altogether there are only a very small number of biocides which have an adequately high water-solubility for use in aqueous solutions so that only a limited number of possibly suitable biocides are available for use e.g. in diagnostic tests. Even these few biocides frequently interact undesirably with test components such as e.g. proteins so that it is often difficult for a test developer to find a suitable biocide at all. There is therefore a great need for alternative water-soluble biocides.

In DE-OS 40 22 878.9 a combination of at least two water-soluble preservatives is proposed which are suitable for preserving diagnostic tests. However, with regard to the common development of resistant microorganisms, it is absolutely necessary to be able to fall back on a larger selection of suitable biocides.

It has been known for a long time that cyclodextrins and cyclodextrin derivatives can form inclusion compounds with numerous molecules (see e.g. J. Szejtli, Cyclodextrins in Diagnostics, "Kontakte" (Darmstadt) 1988 (1), 31–36; J. Szejtli, Cyclodextrins in Drug Formulations: Part I and Part II, Pharmaceutical Technology Internation, February 1991, p. 15–23 and March 1991, p. 16–24; W. Saenger, "Angew. Chem. 92 (1980), p. 343–361).

The use of such inclusion compounds is known from the literature for the "microencapsulation" of sensitive aromatics, pharmaceutical agents, herbicides and insecticides. This often leads to more advantageous properties of the included substances (e.g. stabilization, change in the chemical reactivity and more favourable physicochemical properties). Inclusion in cyclodextrins is also known to increase the solubility of compounds which are sparingly soluble in water.

Inclusion compounds of biocides in cyclodextrins are also known. Thus the inclusion complex of iodine in β-cyclodextrin described in JP 75-23854 and JP 52-015809 has antiseptic and fungicide properties.

The inclusion of sparingly water-soluble substances such as sorbic acid and benzoic acid is for example known from JP 53-113017 for the preservation of foods over a wide pH range.

However, the inclusion of sparingly water-soluble biocides in cyclodextrins in order to increase the water-solubility of the biocides in such a way that they can be used directly to preserve aqueous systems and in particular diagnostic test solutions is not known from the prior art.

Thus the present invention concerns a complex of cyclodextrin and an organic biocide characterized in that the organic biocide has a maximum water-solubility of 0.15% (w/v) at a temperature of 25° C. The organic biocide preferably has a maximum water-solubility of 0.12% (w/v) and particularly preferably of 0.10% (w/v).

The term "organic biocide" within the sense of the present invention denotes substances with at least one carbon-hydrogen bond. Preferred organic biocides are o-phenylphenol, Densil P [dithio-2,2'-bis(benzmethylamide)], [1,2-benzisothiazolin-3-thion] and methylenebisthiocyanate, cyanate, wherein Proxel and methylenebisthiocyanate are most preferred. Further examples of suitable organic biocides are hydroxyquinoline, Carbendazim [-methoxycarbonylamino-benzimidazol] or Dazomet[3,5-dimethyltetrahydro-1,3,5-thiodiazin-2-thion].

It was found that the complexes of cyclodextrins and sparingly soluble organic biocides have excellent biocidal properties and practically do not interact at all with proteins in aqueous solution. This is all the more surprising since non-complexed biocides interact in many cases to a greater or lesser degree with proteins in aqueous solutions which, however, is for example very undesirable in diagnostic tests since this interferes with the test.

In addition it was surprisingly found that the complexes according to the invention are sometimes more effective than the free biocide. Thus for example the inclusion complex of methylenebisthiocyanate is 10-fold more active than the non-included active substance with respect to content of active substance.

The biocide is complexed by inclusion of the biocide in the cyclodextrin and the following equilibrium is present:

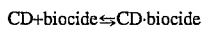

The concentration of the free biocide depends on the dissociation constant $K_D$. If the equilibrium of this reaction lies too far to the left side then the complex would be unstable and the sparingly water-soluble biocide would precipitate. The complexes according to the invention have such a high stability that a considerable improvement of the solubility of the biocide is observed.

The second component of the complex according to the invention is cyclodextrin. The unsubstituted α, β and γ cyclodextrins can be used, however, for reasons of water-solubility of the complexes, it is preferable to use derivatized cyclodextrins with a higher water-solubility. Cyclodextrins substituted with $C_1$–$C_4$ hydroxyalkyl groups or/and $C_1$–$C_4$ alkyl groups are preferably used for this purpose. Such cyclodextrins are commercially available for example from the "Wacker Chemie GmbH" (Munich, Germany). Specific examples are hydroxypropyl, hydroxyethyl or methyl-substituted cylcodextrins such as hydroxypropyl-γ-cyclodextrin (MS=0.6), hydroxypropyl-α-cyclodextrin (MS=0.6), hydroxypropyl-β-cyclodextrin (MS=0.6 or 0.9), hydroxyethyl-β-cyclodextrin (MS=0.6 or 1.0) or methyl-β-cyclodextrin (DS=1.8). In this connection a value of 0.6 for the molar substitution (MS) denotes that on average 60% of all sugar residues in the cyclodextrin are provided with a corresponding substituent. A degree of substitution (DS) of 1.8 denotes that on average 1.8 substituents (e.g. methyl groups) are present on a single sugar residue.

The new complexes can for example be produced in an aqueous solution of the respective cyclodextrin in a well-known manner by adding the biocides to be included to an aqueous solution of the respective cyclodextrin and heating for a longer period. The insoluble biocidal substance slowly dissolves in this process in which in each case the lesser dissolved portion is apparently immediately included in the complex.

Furthermore the complexes according to the invention can be produced in an organic solvent in which case the solvent is removed again for example by evaporation after formation of the complex. Finally the complexes according to the invention can also be produced by intensive mixing of the two components with addition of a small amount of water. In this connection it should be pointed out that in principle the inclusion compounds according to the invention can be prepared according to methods which have already been described for the production of cyclodextrin complexes. The present invention therefore also includes a process for the production of the complexes characterized in that suitable amounts of a cyclodextrin and of an organic biocide are added to an aqueous or organic solvent system or are intensively mixed together and the complex which forms is isolated from the reaction mixture.

The present invention in addition concerns the use of the new complexes to preserve aqueous solutions wherein the aqueous solution preferably contains proteins. It is in particular preferred that the solution contains enzymatically active proteins and/or immunologically active proteins (e.g. antibodies or antibody fragments) which are usually present in a diagnostic test solution. The term "diagnostic test solution" means that the solution is intended for the determination of an analyte by enzymatic, immunological or other (e.g. affinity binding) methods. The diagnostic test solution is preferably intended for the determination of a biological analyte in a body fluid (e.g. blood, plasma or urine).

The present invention also concerns a diagnostic test solution which is characterized in that it contains a complex according to the invention. The concentration of the complex in the test solution depends on the biocidecyclodextrin complex used in each case and on the intended application. It has in general proven to be expedient to use complexes at concentrations of 0.1 µg/ml to 50 mg/ml, preferably 1 µg/ml to 10 mg/ml.

Finally the invention in addition concerns a preserved diagnostic test kit comprising test reagents and at least one biocide-cyclodextrin complex according to the invention. The complex according to the invention can be added to the buffer as well as to the respective test reagent in the test kit. However, it has proven to be expedient to add the complex to the test reagents and buffer solutions simultaneously. The test reagents are usually biologically active proteins and in particular enzymes or/and antibodies.

The complex according to the invention has proven to be particularly suitable for those tests which contain proteins, in particular enzymatically active proteins, antibodies or/and protein hormones, substrates for enzymes, hormones, in particular T3, T4 and steroids or/and antigens or haptens.

It is intended to further elucidate the invention by the following examples.

EXAMPLE 1

Production of the inclusion complexes

The commercially available cyclodextrins (Wacker GmbH, Munich, Germany) Alpha W 6 HP 0.9 (hydroxypropyl-α-cyclodextrin, MS=0.9), Beta W 7 M 1.8 (methyl-β-cyclodextrin, DS=1.8) and Gamma W 8 HP 0.6 (hydroxypropyl-γ-cyclodextrin, MS=0.6) were used as cyclodextrins.

Compounds with a good biocidal action and a low water-solubility were selected as biocides. In particular, inclusion complexes of o-phenylphenol, methylenebisthiocyanate, Densil P and Proxel were produced. The respective biocides are all commercially available. Proxel and Densil P which are only on the market as an aqueous dispersion, were previously isolated as a pure substance for the complexation. The complexes were then produced by heating the two components in a ratio of about 1 part by weight biocide to 9 parts by weight cyclodextrin in water and subsequently removing the water by distillation.

EXAMPLE 2

Determination of the biocidal action of the complexes according to the invention The spectrum of activity of the individual biocide inclusion complexes was determined on bacteria (gram-positive and gram-negative strains), yeasts and fungi (see Table 1). The values are stated as MIC values (=minimum inhibitory concentration) in mg/ml. When comparing the values in Table 1 it should be noted that the amount of active substance in the complex compounds is <10% so that the MIC values for the complexes must be multiplied by a factor of ca. 0.1 in order to be directly comparable with the MIC values for the free biocides.

The determination of the growth of the microorganisms was carried out on M121 medium (Sabouraud, 2% maltose nutrient agar (Merck)) for yeasts and fungi and on M130 medium (standard I nutrient agar (Merck)) for bacteria after 72 hours at 28° C. The amount of active substance in the CD inclusion compounds is less than 10%.

TABLE 1

| | MIC of included and free biocides (mg/ml) | | | | | |
|---|---|---|---|---|---|---|
| | Organism | | | | | |
| Biocide | 1 | 2 | 3 | 4 | 5 | 6 |
| o-phenyl-phenol | 1.25 | 1.25 | 1.25 | 1.25 | 0.3 | 0.6 |
| γ-CD-HP 0.6 o-phenyl-phenol | 5.0 | 5.0 | 10.0 | 5.0 | 1.25 | 2.5 |
| methylenebis- | 0.075 | 0.0175 | <0.04 | <0.04 | 0.02 | 0.02 |

TABLE 1-continued

| | MIC of included and free biocides (mg/ml) | | | | | |
|---|---|---|---|---|---|---|
| | Organism | | | | | |
| Biocide | 1 | 2 | 3 | 4 | 5 | 6 |
| thiocyanate | | | | | | |
| β-CD-methyl-methylenebisthiocyanate | 0.075 | 0.15 | <0.04 | 0.15 | 0.04 | 0.04 |
| Densil P | <0.04 | <0.04 | 0.3 | 0.075 | <0.04 | 0.6 |
| β-Cd-methyl-Densil P | 0.075 | 0.3 | 0.6 | 0.3 | 0.15 | 0.3 |
| Proxel | <0.04 | <0.04 | <0.04 | <0.04 | 0.075 | 0.04 |
| α-CD-HP-0.9 Proxel | 0.3 | 1.25 | 0.6 | 0.6 | 1.25 | 0.6 |

Organisms:
1 = Bacillus subtilis (gram +)
2 = Staphylococcus aureus (gram +)
3 = Pseudomonas fluorescens (gram −)
4 = Escherichia coli (gram −)
5 = Aspergillus oryzae (fungus)
6 = Candida albicans (yeast)

Table 1 shows that the inclusion complexes of o-phenylphenol, Densil P, in particular methylenebisthiocyanate and also in some cases of Proxel are much more active with respect to content of active substance (taking into account the amount of active substance in the complexes of ca. 10%) than the free biocides.

Table 2 shows a further determination of MIC values for biocide-cyclodextrin complexes on four different germ mixtures of microorganisms (yeasts, fungi, bacteria 1, bacteria 2). The test procedure was as in example 1 and the requirement was a reduction in the titre of the microorganisms of 2 powers of 10 within 14 days and a further power of 10 until the end of the experiment after 6 weeks for bacteria and a decrease in titre of 2 powers of 10 within the entire experimental time course (6 weeks) for yeasts and fungi.

In this case the amount of biocide in the cyclodextrin inclusion complexes is also ca. 10%.

TABLE 2

Determination of the MIC value for included biocides

| | MIC value (mg/ml) | | | |
|---|---|---|---|---|
| Biocide | yeasts | fungi | bact.1 | bact.2 |
| α-CD-HP0.9-Carbendazim | 25 | 50 | 12.5 | 6 |
| α-CD-HP0.9-Dazomet | 12.5 | 25 | 25 | >50 |
| α-CD-HP0.9-Proxel | 1.5 | 1.5 | 1.5 | 1.5 |
| β-CD-methyl-Carbendazim | 25 | 50 | 12.5 | 6 |
| β-CD-methyl Densil P | 0.2 | 2 | 0.6 | 1 |
| β-CD-methyl-hydroxyquinoline | 6 | 6 | >50 | 50 |
| β-CD-methyl-methylene-bisthiocyanate | 0.2 | 0.02 | >0.2 | >2.5 |
| β-CD-methyl Proxel | 1.5 | 1.5 | 3 | 3 |
| γ-CD-HP0.6-Carbendazim | 12.5 | 12.5 | 6 | 6 |
| γ-CD-HP0.6-Dazomet | 3 | 6 | 12.5 | 25 |
| γ-CD-HP0.6-hydroxyquinoline | 3 | 6 | 25 | 50 |
| γ-CD-HP0.6-o-phenylphenol | 6 | 6 | 10 | 10 |

This table shows that the complexes according to the invention are active against microorganisms not only in the case of the aforementioned biocides but also in the case of other biocides (such as e.g. hydroxyquinoline, Carbendazim, Dazomet). The microorganism mixtures for the preserving test were as follows:

a) Bacteria 1:
Bacillus subtilis, Escherichia coli, Pseudomonas aeruginosa, Staphylococcus aureus and Enterococcus faecalis.

b) Bacteria 2:
Aeromonas spec., Alcaligenes spec., Flavobacter spec., Proteus vulgaris, Pseudomonas aeruginosa, Pseudomonas fluorescens, Pseudomonas putida.

c) Yeasts:
Candida albicans, Rhodotorula rubra, Penicillium glabrum.

c) Fungi:
Aspergillus oryzae, Mucor racemosus.

EXAMPLE 3

Interaction with proteins

Since enzymes and other proteins are often used for example in diagnostic tests, it is desirable that the biocide-cyclodextrin complex does not interact with the protein. The interaction with proteins was determined by measuring the inhibitory concentration (mg/ml) of the biocide on enzyme tests (lactate dehydrogenase (LDH)) or on immunological tests (albumin in urine (MAU)) (see Table 3).

TABLE 3

| | Amount of biocide per ml mixture | Residual activity | |
|---|---|---|---|
| Biocide | mg/ml | LDH*) | MAU**) |
| α-CD-HP$_{0.9}$ Proxel | 1.5 | 104% | |
| | 3.0 | 104% | |
| | 6.0 | 100% | 94% |
| β-CD-methyl-Densil P | 0.05 | 108% | |
| | 0.2 | 108% | |
| | 0.4 | 112% | |
| | 1.0 | 112% | 93% |
| | 2.0 | | 103% |
| β-CD-methyl-Proxel | 0.7 | 110% | |
| | 1.5 | 110% | |
| | 3.0 | 110% | |
| | 6.0 | 105% | 94% |
| β-CD-methyl-methylenebisthiocyanate | 1.0 | | 103% |
| | 2.0 | | 99% |
| | 2.5 | 104% | |
| γ-CD-HP$_{0.6}$-o-phenylphenol | 3.0 | 104% | |
| | 6.0 | 122% | |
| | 10.0 | 100% | 94% |

*) LDH

The test was carried out in semimicro cuvettes at T=25° C. (λ=366 nm).

| Test mixture: | 0.8 ml | 100 mmol/l Tris HCl, pH 7.0 |
|---|---|---|
| | 0.1 ml | 50 mmol/l pyruvate |
| | 0.1 ml | 5 mmol/l NADH |

10 ng LDH (pig, Boehringer Mannheim GmbH, Id. No. 003565) were added to this.

The 100% value was determined without addition of biocide, then the biocide was dissolved in the test buffer at the concentrations stated in each case and the enzymatic activity was determined.

**) Tina quant albumin in urine (MAU)

The test was carried out according to the instructions on the package insert of the commercial test (Boehringer Mannheim, Order No. 1 203 622). The enzymatic activity without biocide addition was determined as the 100% value. Then the biocide was dissolved in the test buffer at the stated concentrations in each case and the enzymatic activity was determined.

We claim:

1. A complex of cyclodextrin derivatized to have a higher water solubility and an organic biocide, wherein the cyclodextrin is derivatized by a group selected from the group consisting of $C_1$–$C_4$ hydroxyalkyl groups, $C_1$–$C_4$ alkyl groups and a combination of $C_1$–$C_4$ hydroxyalkyl groups and $C_1$–$C_4$ alkyl groups and wherein the organic biocide is selected from the group consisting of dithio-2,2'-bis(benzmethylamide), 1,2-benzisothiazolin-3-thion and methylenebisthiocyanate.

2. The complex according to claim 1, wherein the cyclodextrin is derivatized by a group selected from the group consisting of hydroxypropyl groups, hydroxyethyl groups, methyl groups and combinations of hydroxypropyl groups, hydroxyethyl groups, and methyl groups.

3. A diagnostic test solution, comprising at least one complex of cyclodextrin derivatized to have a higher water solubility, and an organic biocide selected from the group consisting of dithio-2,2'-bis(benzmethylamide), 1,2-benzisothiazolin-3-thion and methylenebisthiocyanate, in combination with a solution for the determination of an analyte, wherein said solution comprises a biologically active protein.

4. The diagnostic test solution according to claim 3, wherein said complex is present at a concentration of 0.1 μg/ml to 50 mg/ml.

5. The diagnostic test solution according to claim 4, wherein said complex is present at a concentration of 0.1 μg/ml to 10 mg/ml.

6. A preserved diagnostic test kit, comprising the following components:

at least one complex of cyclodextrin derivatized to have a higher water solubility and an organic biocide selected from the group consisting of dithio-2,2'-bis-(benzmethylamide), 1,2-benzisothiazolin-3-thion and methylenebisthiocyanate, a buffer, and a test reagent which comprises a biologically active protein.

7. The kit according to claim 6, wherein said biologically active protein is selected from the group consisting of an enzyme and an antibody.

8. A method for preserving a diagnostic test solution comprising adding at least one complex of cyclodextrin derivatized to have a higher water solubility and an organic biocide selected from the group consisting of o-phenylphenol, dithio-2,2'-bis(benzmethylamide), 1,2-benzisothiazolin-3-thion and methylenebisthiocyanate, to said diagnostic test solution, wherein said diagnostic test solution comprises a biologically active protein.

9. The method according to claim 8, wherein the organic biocide is methylenebisthiocyanate.

10. The method according to claim 8, wherein the cyclodextrin is derivatized by a group selected from the group consisting of $C_1$–$C_4$ hydroxyalkyl groups, $C_1$–$C_4$ alkyl groups and a combination of $C_1$–$C_4$ hydroxyalkyl groups and $C_1$–$C_4$ alkyl groups.

11. The method according to claim 10, wherein the cyclodextrin is derivatized by a group selected from the group consisting of hydroxypropyl groups, hydroxyethyl groups, methyl groups and combinations of hydroxypropyl groups, hydroxyethyl groups, and methyl groups.

* * * * *